(12) United States Patent
Kristo

(10) Patent No.: US 12,255,015 B1
(45) Date of Patent: Mar. 18, 2025

(54) DEVICE WITH SUPPLEMENTAL MAGNET SET

(71) Applicant: Cochlear Limited, Macquarie University (AU)

(72) Inventor: Stefan Kristo, Molnlycke (SE)

(73) Assignee: Cochlear Limited, Macquarie University (AU)

(*) Notice: Subject to any disclaimer, the term of this patent is extended or adjusted under 35 U.S.C. 154(b) by 963 days.

(21) Appl. No.: 17/225,302

(22) Filed: Apr. 8, 2021

Related U.S. Application Data

(60) Provisional application No. 63/010,906, filed on Apr. 16, 2020.

(51) Int. Cl.
*A61N 2/00* (2006.01)
*H01F 7/02* (2006.01)
*H04R 25/00* (2006.01)
*A61F 2/18* (2006.01)

(52) U.S. Cl.
CPC .......... *H01F 7/02* (2013.01); *A61F 2002/183* (2013.01); *A61F 2250/0001* (2013.01); *A61N 2/00* (2013.01); *H04R 25/65* (2013.01); *H04R 2460/13* (2013.01)

(58) Field of Classification Search
CPC .................................................. A61N 2/00–12
See application file for complete search history.

(56) References Cited

U.S. PATENT DOCUMENTS

| | | | |
|---|---|---|---|
| 2017/0078808 A1* | 3/2017 | Kennes | H04R 25/606 |
| 2018/0160241 A1* | 6/2018 | Gustafsson | H04R 25/606 |
| 2020/0092632 A1* | 3/2020 | Higgins | H04R 25/70 |
| 2020/0330777 A1* | 10/2020 | Smith | H04R 25/00 |

* cited by examiner

*Primary Examiner* — Thaddeus B Cox
(74) *Attorney, Agent, or Firm* — Edell, Shapiro & Finnan, LLC

(57) ABSTRACT

Examples disclosed herein are relevant to a wearable device configured to selectively receive a primary magnet set selected from among multiple primary magnet sets of varying magnetic strengths. A supplemental magnet set is used with the wearable device to supplement the selected primary magnet set to increase a strength of a magnetic connection. The wearable device can selectively couple with a selected cover. The cover can be an accommodating cover configured to accommodate the at least one supplemental magnet set or a non-accommodating cover for use as the selected cover when a supplemental magnet set is not being used.

20 Claims, 10 Drawing Sheets

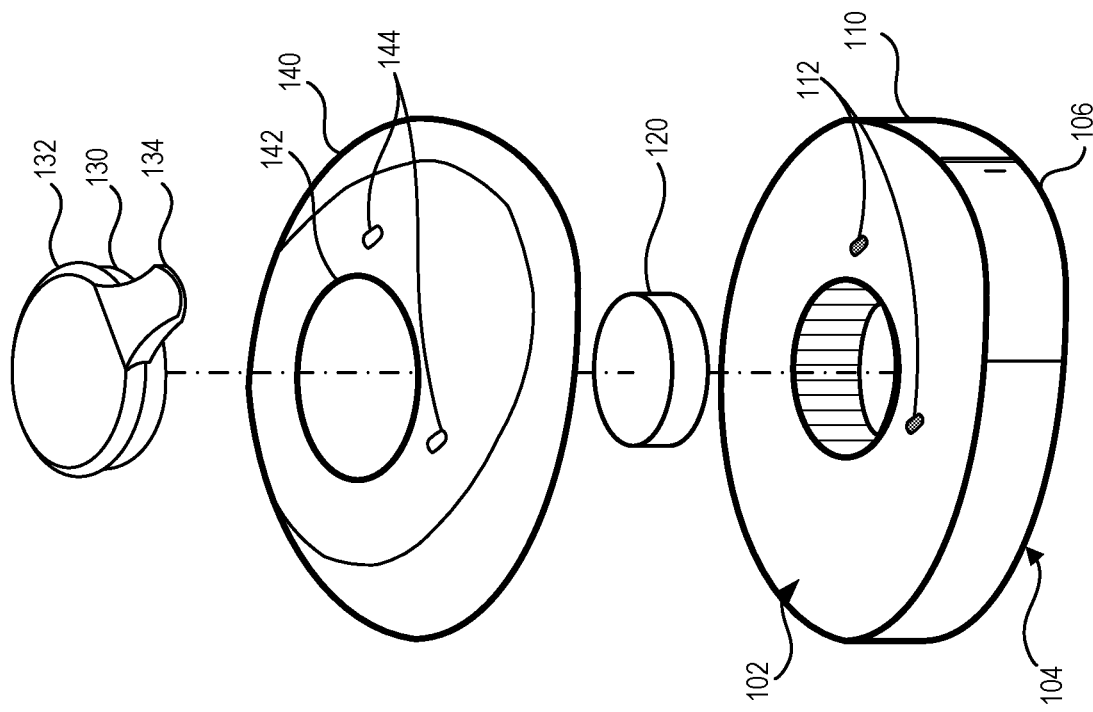
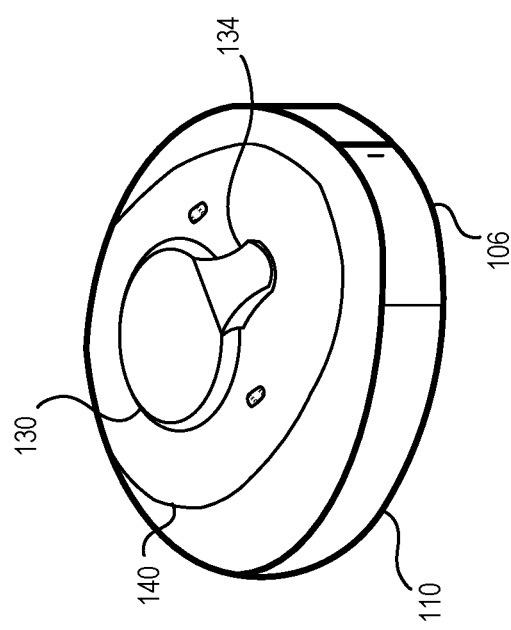

600

```
┌─────────────────────────────────────────────┐         ┌──────────┐
│ ESTABLISHING A FIRST MAGNETIC CONNECTION    │    ⎫    │  FIRST   │
│ BETWEEN AN IMPLANTED MAGNET SET AND A       │    ⎬    │ MAGNETIC │
│ PRIMARY MAGNET SET 610                      │    ⎭    │CONNECTION│
└─────────────────────────────────────────────┘         │   612    │
                       │                                └──────────┘
                       ▼
┌─────────────────────────────────────────────┐
│ SUPPLEMENTING THE PRIMARY MAGNET SET        │
│ WITH A SUPPLEMENTAL MAGNET SET 620          │
│                                             │
│  ┌ ─ ─ ─ ─ ─ ─ ─ ─ ─ ─ ─ ─ ─ ─ ─ ─ ─ ─ ┐   │
│                                             │
│  │           FIG. 6B                   │   │
│                                             │
│  └ ─ ─ ─ ─ ─ ─ ─ ─ ─ ─ ─ ─ ─ ─ ─ ─ ─ ─ ┘   │
└─────────────────────────────────────────────┘
                       │
                       ▼
┌─────────────────────────────────────────────┐         ┌──────────┐
│ ESTABLISHING A SECOND MAGNETIC CONNECTION   │    ⎫    │  SECOND  │
│ BETWEEN THE IMPLANTED MAGNET SET AND THE    │    ⎬    │ MAGNETIC │
│ PRIMARY MAGNET SET AS SUPPLEMENTED BY THE   │    ⎭    │CONNECTION│
│ SUPPLEMENTAL MAGNET SET 630                 │         │   632    │
└─────────────────────────────────────────────┘         └──────────┘
```

```
┌─────────────────────────────────────────────────┐
│         REMOVING A FIRST COVER 622              │
└─────────────────────────────────────────────────┘
                    │
       ┌────────────┼
       ▼            │
┌──────────────────┐│
│ SELECTING A SECOND COVER FROM │
│ A PLURALITY OF SUPPLEMENTAL   │
│ COVERS EACH ASSOCIATED WITH A │
│ DIFFERENT MAGNETIC STRENGTH 623│
└──────────────────┘│
       │            │
       ▼            ▼
┌─────────────────────────────────────────────────┐
│         APPLYING A SECOND COVER 624             │
└─────────────────────────────────────────────────┘

┌─────────────────────────────────────────────────┐
│ SELECTING THE SUPPLEMENTAL MAGNET SET FROM A PLURALITY OF │
│        SUPPLEMENTAL MAGNET SETS 625             │
└─────────────────────────────────────────────────┘

┌─────────────────────────────────────────────────┐
│ DISPOSING THE SUPPLEMENTAL MAGNET SET AT LEAST PARTIALLY WITHIN │
│   AN OPENING DEFINED BY THE SECOND COVER 626    │
└─────────────────────────────────────────────────┘

┌─────────────────────────────────────────────────┐
│ RETAINING THE SUPPLEMENTAL MAGNET SET BY ESTABLISHING │
│ A MAGNETIC CONNECTION BETWEEN THE SUPPLEMENTAL MAGNET SET │
│        AND THE PRIMARY MAGNET SET 627           │
└─────────────────────────────────────────────────┘

┌─────────────────────────────────────────────────┐
│ RETAINING THE SUPPLEMENTAL MAGNET SET BY ESTABLISHING A │
│         MECHANICAL CONNECTION 628               │
└─────────────────────────────────────────────────┘

┌─────────────────────────────────────────────────┐
│ REMOVING THE SUPPLEMENTAL MAGNET SET BY MANIPULATING A GRIP 629 │
└─────────────────────────────────────────────────┘
```

FIG. 6B

DEVICE WITH SUPPLEMENTAL MAGNET SET

BACKGROUND

Field of the Invention

The present invention relates generally to wearable devices.

Related Art

Medical devices have provided a wide range of therapeutic benefits to recipients over recent decades. Medical devices can include internal or implantable components/devices, external or wearable components/devices, or combinations thereof (e.g., a device having an external component communicating with an implantable component). Medical devices, such as traditional hearing aids, partially or fully-implantable hearing prostheses (e.g., bone conduction devices, mechanical stimulators, cochlear implants, etc.), pacemakers, defibrillators, functional electrical stimulation devices, and other medical devices, have been successful in performing lifesaving and/or lifestyle enhancement functions and/or recipient monitoring for a number of years.

The types of medical devices and the ranges of functions performed thereby have increased over the years. For example, many medical devices, sometimes referred to as "implantable medical devices," now often include one or more instruments, apparatus, sensors, processors, controllers or other functional mechanical or electrical components that are permanently or temporarily implanted in a recipient. These functional devices are typically used to diagnose, prevent, monitor, treat, or manage a disease/injury or symptom thereof, or to investigate, replace or modify the anatomy or a physiological process. Many of these functional devices utilize power and/or data received from external devices that are part of, or operate in conjunction with, implantable components.

SUMMARY

In an example, there is an apparatus comprising: a wearable device having a primary magnet set of one or more magnets; a supplemental magnet set having one or more magnets and being configured to be selectively disposed proximate the primary magnet set to enhance a magnetic strength; and a cover configured to couple with the wearable device to accommodate the supplemental magnet set.

In another example, there is a kit comprising: a wearable device configured to selectively receive a selected primary magnet set; multiple primary magnet sets of varying magnetic strengths for use with the wearable device as the selected primary magnet set; and at least one supplemental magnet set for use with the wearable device to supplement the selected primary magnet set.

In yet another example, there is a method comprising: establishing a first magnetic connection between an implanted magnet set and a primary magnet set; supplementing the primary magnet set with a supplemental magnet set; and establishing a second magnetic connection between the implanted magnet set and the primary magnet set as supplemented by the supplemental magnet set, wherein the second magnetic connection is stronger than the first magnetic connection.

BRIEF DESCRIPTION OF THE DRAWINGS

Embodiments of the present invention are described herein in conjunction with the accompanying drawings, in which:

FIG. 1 illustrates a perspective view of a wearable device having a supplemental magnet set.

FIG. 2 illustrates an exploded view of the wearable device of FIG. 1.

FIG. 6, which is made up of FIG. 6A and FIG. 6B illustrates an example method.

DETAILED DESCRIPTION

Figure 3:
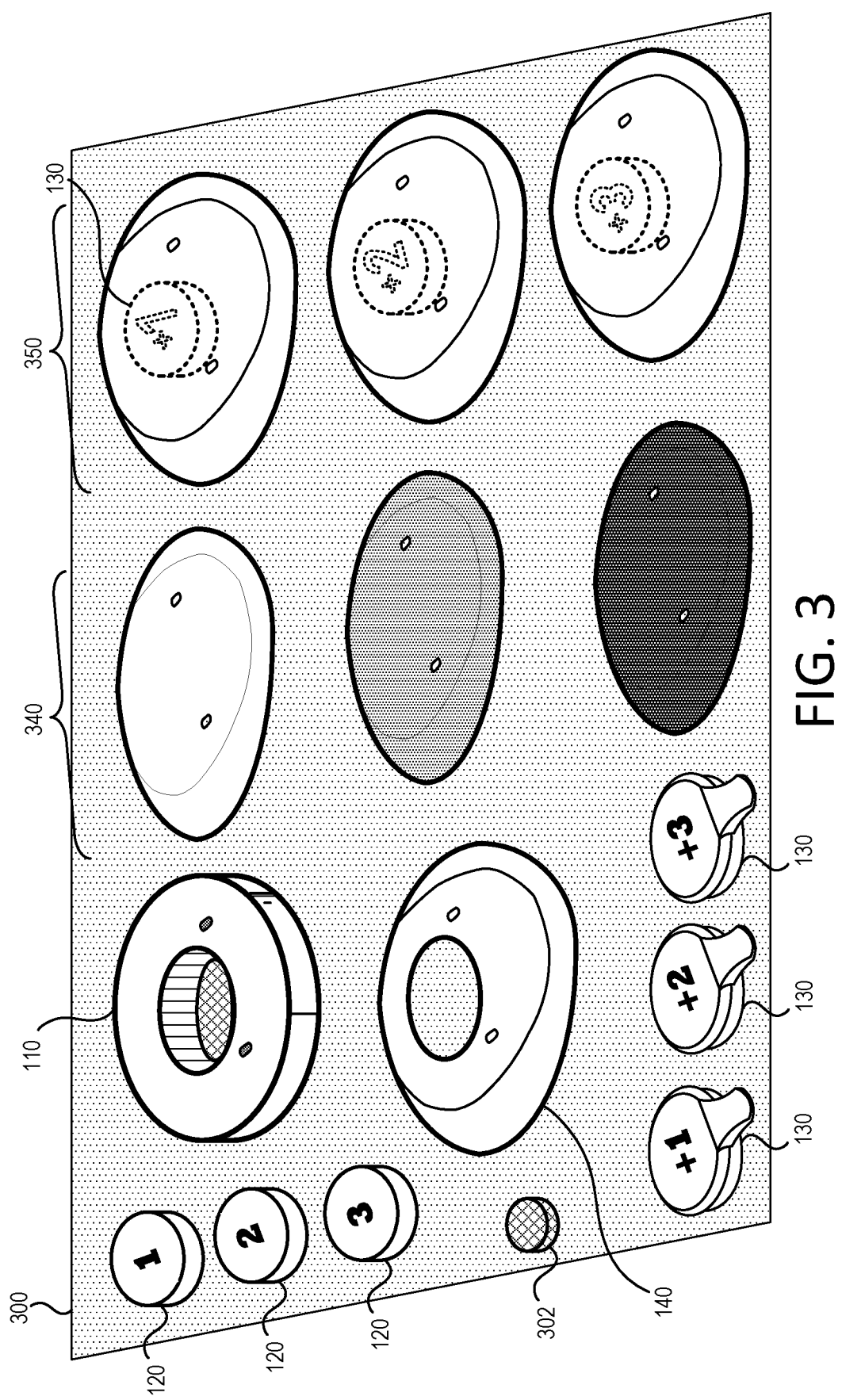
FIG. 3 illustrates an example kit that includes a wearable device, supplemental magnet sets, accommodating covers, and non-accommodating covers.

A magnetic connection can be formed between a magnet set of a wearable external medical device and a magnet set of an implantable medical device. A sufficiently strong magnetic connection can be used to retain the wearable medical device proximate the implantable medical device. A minimum magnetic field strength to reliably retain the wearable medical device can vary depending on various factors, such as a distance between the devices and the activity level of the wearer. The distance between the devices can be affected by a thickness of tissue between the devices, which can vary among recipients of devices. While increased magnetic strength can improve the reliability of the retention, too great of a magnetic field strength can cause discomfort for the recipient. Desired levels of magnetic field strength can vary not only among individuals, but also a same individual can prefer different magnetic field strengths at different times. The magnetic field strength can be changed by exchanging the external magnet set for another external magnet set having desired characteristics. A device can be supplied with different magnet sets for this purpose, but there can be limits that prevent the swapping of an existing magnet for a larger, more powerful magnet to increase magnetic retention strength. For example, a size of a magnet cavity of the wearable device can limit the size of magnets able to be used.

Presented herein are techniques to modify a magnetic strength of a magnetic connection between first and second devices. In particular, the techniques presented herein utilize a supplemental magnet with the wearable device to supplement an existing primary magnet set to, for example, increase a strength of a magnetic connection. The wearable device can be provided with an accommodating cover configured to accommodate/house the at least one supplemental magnet set, such as by providing an opening that exposes the primary magnet set and that can accommodate the supplemental magnet set. Experimental results provided herewith indicate that the disclosed use of a supplemental magnet set can improve the strength of a magnetic connection. An example implementation is shown in FIGS. 1 and 2.

Example Implementation

FIG. 1 and FIG. 2 show respective perspective and exploded views of a wearable device 110. As illustrated, the wearable device 110 includes a primary magnet set 120, a supplemental magnet set 130, and a cover 140, among other components and features.

The wearable device 110 can be a wearable medical device. In an example, the wearable device 110 can be an auditory prosthesis sound processor wearably retained proximate an implanted component, though the wearable device 110 can take other forms such as is described in FIGS. 7-10. In some examples, the wearable device 110 can be a wearable coil that is connectable to another device (e.g., a behind-the-ear device). The wearable device 110 can include one or more components, such as one or more microphones 112, as well as a battery door 106 that covers a battery receptacle. Portions of the wearable device 110 can be referred to with respect to a front and back of the device 110. The back of the device 110 can be a portion of the device 110 that faces or contacts the recipient's skin when the wearable device 110 is worn by the recipient. The front of the device 110 can be a portion that faces away from the recipient's skin when the device 110 is worn by the recipient. The front of the device 110 can be opposite the back of the device 110.

Figure 4:
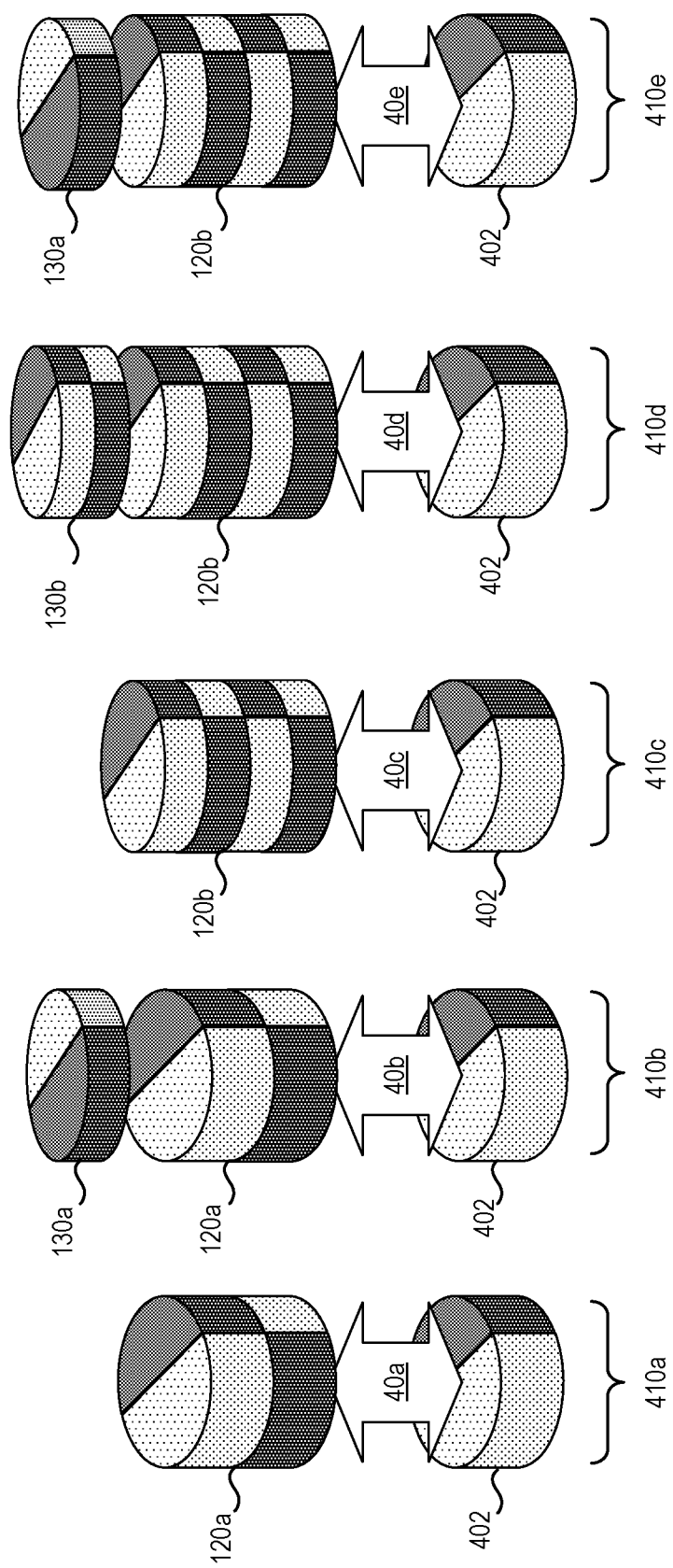
FIG. 4 illustrates example magnet configurations and associated magnetic connections.

The primary magnet set 120 and the supplemental magnet set 130 can be sets of one or more magnets. The primary magnet set 120 can be a set configured to be the primary magnetic set for the device 110. For instance, the primary magnet set 120 can be configured (e.g., sized and shaped) to fit within a magnet receptacle of the wearable device 110. The supplemental magnet set 130 can be a set configured to be selectively disposed proximate the primary magnet set 120 to enhance a magnetic strength. Example implementations of primary magnet set 120 and supplemental magnet set 130 are shown in FIG. 4. The primary magnet set 120 and the supplemental magnet set 130 can each include axially-magnetized magnets, transversely magnetized magnets (e.g., diametrically or radially magnetized magnets), other configurations, or combinations thereof. The primary magnet set 120 and the supplemental magnet set 130 can each include a variety of numbers of magnetic poles, such as at least four magnetic poles (e.g., via a magnet assembled to have multiple magnetic poles or by combinations of separate magnets). For ease of understanding, the magnet sets herein are illustrated as being relatively simple (e.g., being uniform in profile), but magnets herein can take any of a variety of forms. For instance, a magnet can be formed as a ring or disk of multiple different magnets arranged in various polarities to result in a particular magnetic flux circuit with another magnet set. Magnets and magnetic sets herein can, for example, take the form of one or more of the magnets or magnet groups described in US 2019/0239007, which was filed Apr. 5, 2019, is titled "Retention Magnet System for Medical Device", and is incorporated herein by reference in its entirety for any and all purposes. Further, the magnet sets herein can have magnets with poles disposed in any of a variety of ways. Examples of multi-pole magnet configurations that can be used with techniques described herein are described in U.S. provisional patent application No. 62/907,044, which is hereby incorporated by reference in its entirety for any and all purposes.

The supplemental magnet set 130 can be disposed in a supplemental magnet case 132 having a grip 134 configured to facilitate removal of the supplemental magnet case 132 from the wearable device 110. The grip 134 can be a protruding tab that can be used to facilitate removal of the supplemental magnet set 130. In an example, the grip 134 can act as a lever configured to help a user break a force of magnetic attraction between the supplemental magnet set 130 and the primary magnet set 120 or a friction fit between the supplemental magnet set 130 and another component. In some examples, the grip 134 can take the form of a flange. The grip 134 can be knurled or have other features to facilitate manipulation by a user.

In some examples, the primary magnet set 120 and the supplemental magnet set 130 can be differentiated based on their respective magnetic strength. The primary magnet set 120 can have a stronger overall magnetic strength than the supplemental magnet set. For example, primary magnet sets 120 can be configured to, by themselves, retain the wearable device 110, while the supplemental magnet set 130 may be unable to retain the wearable device 110 relative to an implanted device by itself. In some examples, the supplemental magnet set 130 can be unable to be used with the wearable device 110 without a modification to the device 110, such as via the use of a cover 140 that accommodates the supplemental magnet set.

The cover 140 can be a component configured to couple with the wearable device 110, such as via a threaded connection, a snap-fit connection, a latching connection, other connections, or combinations thereof. In an example, the cover 140 can couple with a front of the wearable device 110 and take the form of a front faceplate of the wearable device 110 that primarily faces outward. The cover 140 can provide any of a variety of different kinds of functions. In some examples, the cover 140 can be configured to protect the underlying device. In addition or instead, the cover 140 can be a decorative component that is colored or patterned to suit a recipient's preferences (e.g., to match the recipient's hair color). Where the wearable device 110 includes openings (e.g., for the one or more microphones 112 or for ventilation), has certain protruding portions (e.g., a button), or has certain areas that need to remain uncovered (e.g., a light sensor or a charging port), the cover 140 can be configured to not interfere with those components, such as by defining at least one opening or notch. In the illustrated configuration, the device 110 has two microphones 112 and the cover 140 defines two microphone openings 144 that each align with a respective one of the microphones 112 of the device 110 when the cover 140 is coupled with the wearable device 110.

In the illustrated example, the cover 140 is an accommodating cover configured to accommodate the supplemental magnet set 130. The cover 140 can be configured to accommodate the supplemental magnet set 130 in any of a variety of ways. For example, in the illustrated example configuration, the cover 140 defines an opening 142 sized to receive at least a portion of the supplemental magnet set 130. The opening 142 and the device 110 can be so configured that, when the cover 140 is coupled with the wearable device 110, the primary magnet set 120 is at least partially exposed through the opening 142. The supplemental magnet set 130 can be disposed in the opening 142 such that the supplemental magnet set 130 is sufficiently proximate the primary magnet set 120 that the supplemental magnet set 130 is retained in the opening 142 solely by its magnetic connection with the primary magnet set 120.

In addition or instead, the cover 140 can be configured to accommodate the supplemental magnet set 130 by having one or more fasteners configured to mechanically engage with the supplemental magnet set 130. The supplemental magnet set 130 can be configured to be retained to the wearable device 110 by a magnetic connection between the supplemental magnet set 130 and the primary magnet set 120. In addition or instead, the supplemental magnet set 130 can be configured to be retained to the wearable device 110 by a mechanical connection with the cover 140. For example, there can be a threaded connection, a snap-fit connection, a latching connection, other connections, or combinations thereof. The supplemental magnet set 130 (e.g., a case and other components thereof) can be configured to avoid interfering (e.g., covering or blocking) one or more areas of the cover 140 that are configured to remain open (e.g., to accommodate the at least one microphone 144 or other components of the device 110).

In addition or instead, the cover 140 can be configured to accommodate the supplemental magnet set 130 by being sized and shaped (e.g., with a bulge) to accommodate the supplemental magnet set 130 being disposed within or otherwise coupled to the cover 140 such that removing the cover 140 can remove the supplemental magnet set 130 and applying the cover 140 to the device 110 also applies the supplemental magnet set 130 to the device 110. In an example, the cover 140 can define a concavity and the supplemental magnet set 130 can be disposed within the concavity.

In some examples, the wearable device 110 can be provided as part of a kit having multiple different magnetic retention options, such as by having multiple different primary magnet sets 120, supplemental magnet sets 130, and covers 140 from which to choose for use with the device 110. An example of such a kit is shown and described in FIG. 3.

Example Kit

FIG. 3 illustrates an example kit 300 that includes the wearable device 110 as well as other components that can be used with the wearable device 110. The kit 300 can be a packaging of one or more components for use with the wearable device 110. The wearable device 110 can be configured to selectively receive a selected primary magnet set 120. The kit 300 can include multiple different primary magnet sets 120 of varying magnetic strengths (e.g., as indicated by a different number label, with the higher the number the higher the associated magnetic strength) for use with the wearable device 110 as the selected primary magnet set 120. The kit 300 can further include at least one supplemental magnet set 130 for use with the wearable device 110 to supplement the selected primary magnet set 120. In the illustrated example, the kit 300 includes multiple different supplemental magnet sets 130 of varying magnetic strengths for use with the wearable device 110 as a selected supplemental magnet set 130. The wearable device 110 can be configured to couple with a selected cover 140, and the kit 300 can include multiple covers from which to select. For example, the kit 300 can include at least one accommodating cover 140 and at least one non-accommodating cover 340.

The at least one non-accommodating cover 340 can be a cover 140 that is unable to accommodate the at least one supplemental magnet set 130 provided with the kit 300 for use in supplementing the selected primary magnet set 120. Such non-accommodating covers 340 can be used, for example, when a recipient wants to wear the device 110 with a cover 140 but without wanting to use a supplemental magnet set 130. The non-accommodating cover 340 can lack all of the configurations described above that can be used to accommodate the supplemental magnet set 130. For example, while the accommodating covers can include an opening 142 into which a supplemental magnet case 132 can be at least partially received, each of the at least one non-accommodating cover 340 can lack an opening 142 into which a supplemental magnet case 132 can be at least partially received, thereby being unable to accommodate the at least one supplemental magnet set 130.

The at least one accommodating cover 140 can be configured to accommodate the at least one supplemental magnet set 130 when the at least one supplemental magnet set 130 is used to supplement the selected primary magnet set 120. Examples of how the accommodating cover 140 can be configured to accommodate the at least one supplemental magnet set 130 are described above in relation to FIGS. 1 and 2. In some examples, the kit 300 can include multiple different covers 140, each having different colors or patterns to suit a recipient's preferences.

In addition to showing the supplemental magnet set 130 and the accommodating covers 140 as separate components, those components can be combined. For example, the illustrated kit 300 further includes accommodating covers 140 in the form of combination covers 350 having the supplemental magnet set 130 removably or unremovably disposed therein. Thus, the kit 300 includes multiple different combination covers 350 each associated with different magnetic strengths as a result of the supplemental magnet sets 130 associated therewith having different magnetic strengths.

The kit 300 can further include one or more additional components, such as a battery 302. Other components can include, for example, chargers, cleaning kits, locks, clips, securing components, other components, or combinations thereof.

As discussed above, the primary magnet set 120 and the supplemental magnet set 130 can be sets of one or more magnets and take any of a variety of different forms. Example implementations of primary magnet set 120 and supplemental magnet set 130 are shown in FIG. 4. Different implementations can result in different magnetic connection strengths, which is shown in the experimental results of FIG. 5.

Example Magnet Configurations and Experimental Results

FIG. 4 illustrates magnet configurations 410 and associated magnetic connections 40 with light and dark shading being used to illustrate different magnet poles (e.g., the south poles being light shaded and the north poles being dark shaded).

In a first magnet configuration 410a, there is a first primary magnet set 120a having a first magnetic connection 40a with an implanted magnet set 402. The first primary magnet set 120a includes two diametrically magnetized magnets having two poles each. Alternatively, the first primary magnet set 120a can be implemented as one diametrically magnetized magnet having a total of four poles.

In a second magnet configuration 410b, there is the first primary magnet set 120a being supplemented by a first supplemental magnet set 130a and having a second magnetic connection 40b with the implanted magnet set 402. The first supplemental magnet set 130a includes a single diametrically magnetized magnet having two poles.

In a third magnet configuration 410c, there is a second primary magnet set 120b having a third magnetic connection 40c with the implanted magnet set 402. The second primary magnet set 120b two diametrically magnetized magnets having four poles each (in other implementations, four diametrically magnetized magnets having two poles each can be used), for a total of eight poles.

In a fourth magnet configuration 410d, there is the second primary magnet set 120b being supplemented by a second supplemental magnet set 130b and having a fourth magnetic connection 40d with the implanted magnet set 402. The second supplemental magnet set 130b includes one diametrically magnetized four-pole magnet. In other implementations, the second supplemental magnet set 130b can be constructed from two diametrically magnetized two-pole magnets.

In a fifth magnet configuration 410e, there is the second primary magnet set 120b being supplemented by the first supplemental magnet set 130a and having a fifth magnetic connection 40e with the implanted magnet set 402.

Each of the different magnet configurations 410 can result in a different strength of the magnetic connection 40 with the implanted magnet set 402. Example results of an experiment conducted using the different magnet configurations 410 is shown in FIG. 5.

Figure 5:
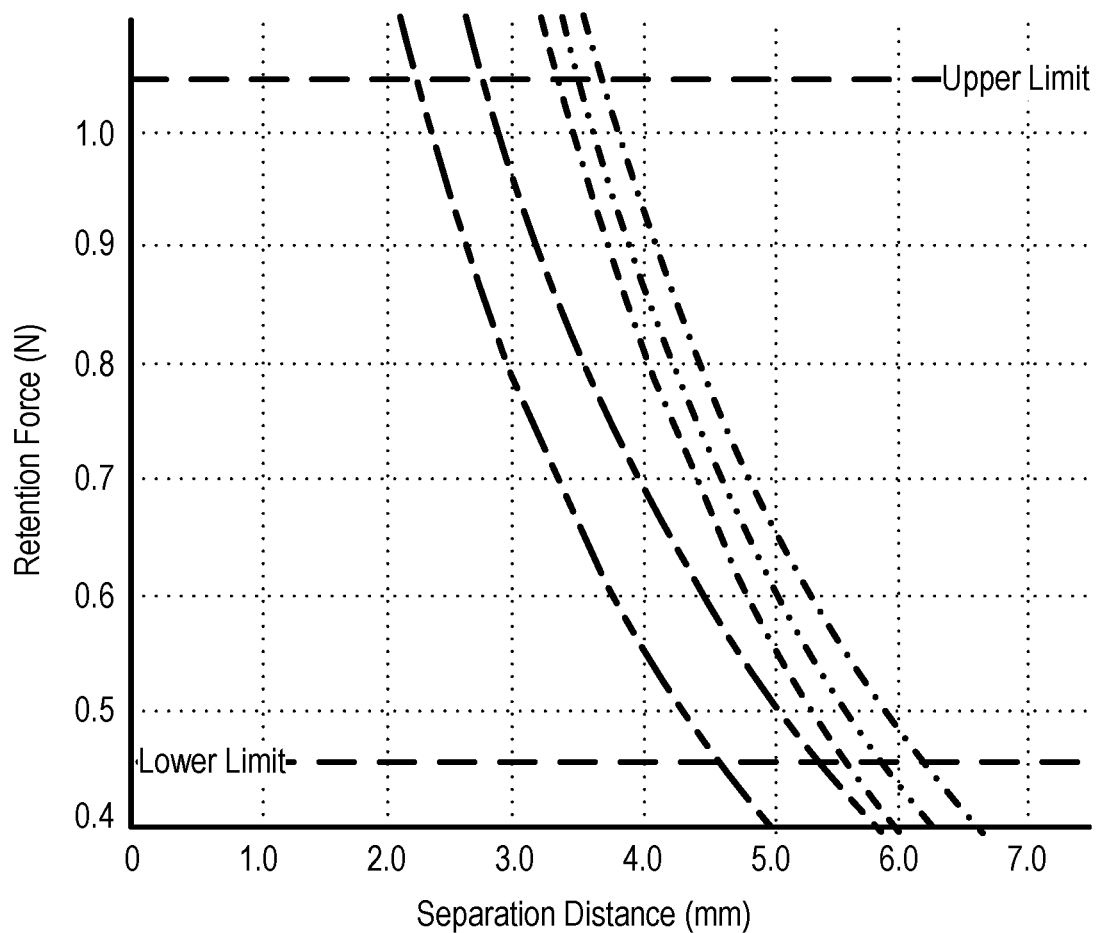
FIG. 5 illustrates a graph showing a comparison of magnetic retention force provided by the magnetic connections of FIG. 4 over a range of distances.

FIG. 5 illustrates a graph showing results of an experiment conducted using the five magnetic configurations 410 described in relation to FIG. 4. The experiment was conducted by gluing the implantable magnet set 402 to an aluminum rod fitted into a lower portion of an INSTRON testing machine. Then a primary magnet set 120 and a supplemental magnet set 130 (if any in the magnet configuration 410) to be tested were glued to a shorter aluminum rod and fitted in an upper portion of the INSTRON testing machine. The retention force of the magnetic connection 40 between the implantable magnet set 402 and the magnet assembly (the primary magnet set 120 as supplemented by a supplemental magnet set 130, if any) was recorded across various distances between the implantable magnet set 402 and the magnet assembly. All of the magnets being tested were constructed from N48 material. As can be seen in the testing results, the use of the supplemental magnet sets 130 increased the force of the magnetic connection 40 compared to a same primary magnet set 120 lacking supplementation.

The graph shows a comparison of magnetic retention force (measured in newtons) provided by the magnet configurations 410 of FIG. 4 over various the various distances (measured in millimeters). The retention force for each is shown relative to an upper retention force limit and a lower retention force limit. The upper limit corresponds to an amount of force above which may cause undesirable effects (e.g., tissue irritation) to a recipient when the implanted magnet set 402 is disposed beneath the recipient's skin and the magnet assembly is worn externally. The lower limit corresponds to an amount of force below which the magnet assembly may be unable to be desirably be retained by the magnetic connection 40 relative to the implanted magnet set 402. In the illustrated chart, the separation distance represents a modification of the magnet-to-magnet distance to compensate for an implant magnet to end of silicone distance and an external magnet to magnet to end of external device distance to better account for real-world conditions.

As shown in the graph, the use of the first supplemental magnet 130a in the second configuration 410b resulted in an approximately 20% increase in retention force for a given distance compared to the first configuration 410a where the second supplemental magnet was not present. The use of the first supplemental magnet 130a and the second supplemental magnet 130b in the fifth configuration 410d and fourth configuration 410e, respectively, resulted in higher retention forces than the third configuration 410c, which lacked a supplemental magnet set 130. Thus, this experiment confirms that the use of a supplemental magnet set 130 can enhance the strength of the magnetic connection 40.

Example Method

FIG. 6, which is made up of FIGS. 6A and 6B, illustrates an example method 600. The method can begin with operation 610.

Operation 610 can include establishing a first magnetic connection 612 between an implanted magnet set 402 and a primary magnet set 120. In some examples, establishing the first magnetic connection 612 can include a recipient wearing the wearable device 110 in which the primary magnet set 120 is disposed. The recipient can do so by bringing the device 110 proximate an area where the implanted magnet set 402 is implanted in the recipient. In some examples, establishing the first magnetic connection 612 includes establishing an inductive power and data connection between a wearable device 110 having the primary magnet set 120 and a device (e.g., an implanted stimulator device) in which the implanted magnet set 402 is disposed. In some examples, during this operation 610, the wearable device 110 can lack a supplemental magnet set 130 and can lack an accommodating cover 140 (e.g., the wearable device 110 may be coupled with a non-accommodating cover 340 instead). Following operation 610, the flow of the method 600 can move to operation 620.

Operation 620 can include supplementing the primary magnet set 120 with a supplemental magnet set 130. As illustrated, operation 620 can include operations 622-629 as shown in FIG. 6B.

Operation 622 can include removing a first cover 140 of the wearable device 110 that houses the primary magnet set 120. For example, the first cover 140 can be a non-accommodating cover 340 or a combination cover 350. Following operation 622, the flow of the process can move to operation 623 or 624. Removing the cover 140 can include, for example, disengaging a fastener holding the first cover 140 in place. For example, the recipient can disengage a snap-fit clip to remove the first cover 140. In some examples, the recipient can open a battery door 106 of the wearable device and then press and lift the cover 140 to remove the cover 140.

Operation 623 can include selecting the second cover 140 from a plurality of supplemental covers 140 (e.g., of the kit 300) that are each associated with a different magnetic strength. For example, the plurality of supplemental covers 140 can each be a combination cover 350 having a different supplemental magnet set 130 that can result in a different magnetic strength. The selecting of the cover 140 can include selecting a cover 140 to result in a desired increase or decrease in magnetic strength. Following operation 623, the flow of the method 600 can move to operation 624.

Operation 624 can include applying a second cover 140 to the device 110. For example, the second cover 140 can be the cover 140 selected in operation 623. The second cover 140 can be, for example, an accommodating cover 140, such as a supplemental cover 350. Applying the second cover 140 can include engaging a fastener to couple the second cover 140 to the device 110. In some examples, a battery door 106 of the device 110 can act as a lock. Applying the second cover 140 can include placing the second cover 140 over the front of the device 110, pressing down on the second cover 140 in one or more locations until the second cover 140 snaps in place. These steps can be performed with the battery door 106 open and the battery door 106 can be closed after the second cover is snapped into place, thereby completing applying the second cover 140 to the device 110 in this example.

Operation 625 can include selecting the supplemental magnet set 130 from a plurality of supplemental magnet sets 130. For example, the supplemental magnet set 130 can be selected based on desired magnetic characteristics. The supplemental magnet set 130 can be selected from the kit 300.

Operation 626 can include disposing the supplemental magnet set 130 at least partially within an opening 142 defined by the second cover 140. For example, the supplemental magnet set 130 can be placed within the opening 142 proximate the primary magnet set 120. In some examples, following operation 626, the flow of the method 600 can move to operation 627.

Operation 627 can include retaining the supplemental magnet set 130 relative to the primary magnet set 120 by establishing a magnetic connection between the supplemental magnet set 130 and the primary magnet set 120.

Operation 628 can include retaining the supplemental magnet set 130 by establishing a mechanical connection. For example, the retaining can be performed by using a fastener. For example, retaining the supplemental magnet set 130 can be performed through the use of a threaded connection, a snap-fit connection, a latching connection, other connections, or combinations thereof.

Operation 629 can include removing the supplemental magnet set 130 by manipulating a grip 134. The recipient can use the grip 134 as a lever to help break a force of magnetic attraction between the supplemental magnet set 130 and the primary magnet set 120. In some examples, the user can grab a flanged or knurled portion of the grip 134 and twist or pull the grip to facilitate removal of the supplemental magnet set 130.

Following operation 620, the flow of the method 600 can move to operation 630 of FIG. 6A.

Operation 630 can include establishing a second magnetic connection 632 between the implanted magnet set and the primary magnet set as supplemented by the supplemental magnet set. The second magnetic connection 632 can be stronger than the first magnetic connection 612 (e.g., result in a magnetic connection having a greater magnetic force). For example, the force of the magnetic connection between the wearable device 110 having the primary magnet set 120 (and lacking the supplemental magnet set 130) and the implanted magnet set 402 can be less than the force of the magnetic connection between the primary magnet set 120 and the supplemental magnet set 130.

Example Devices

Figure 7:
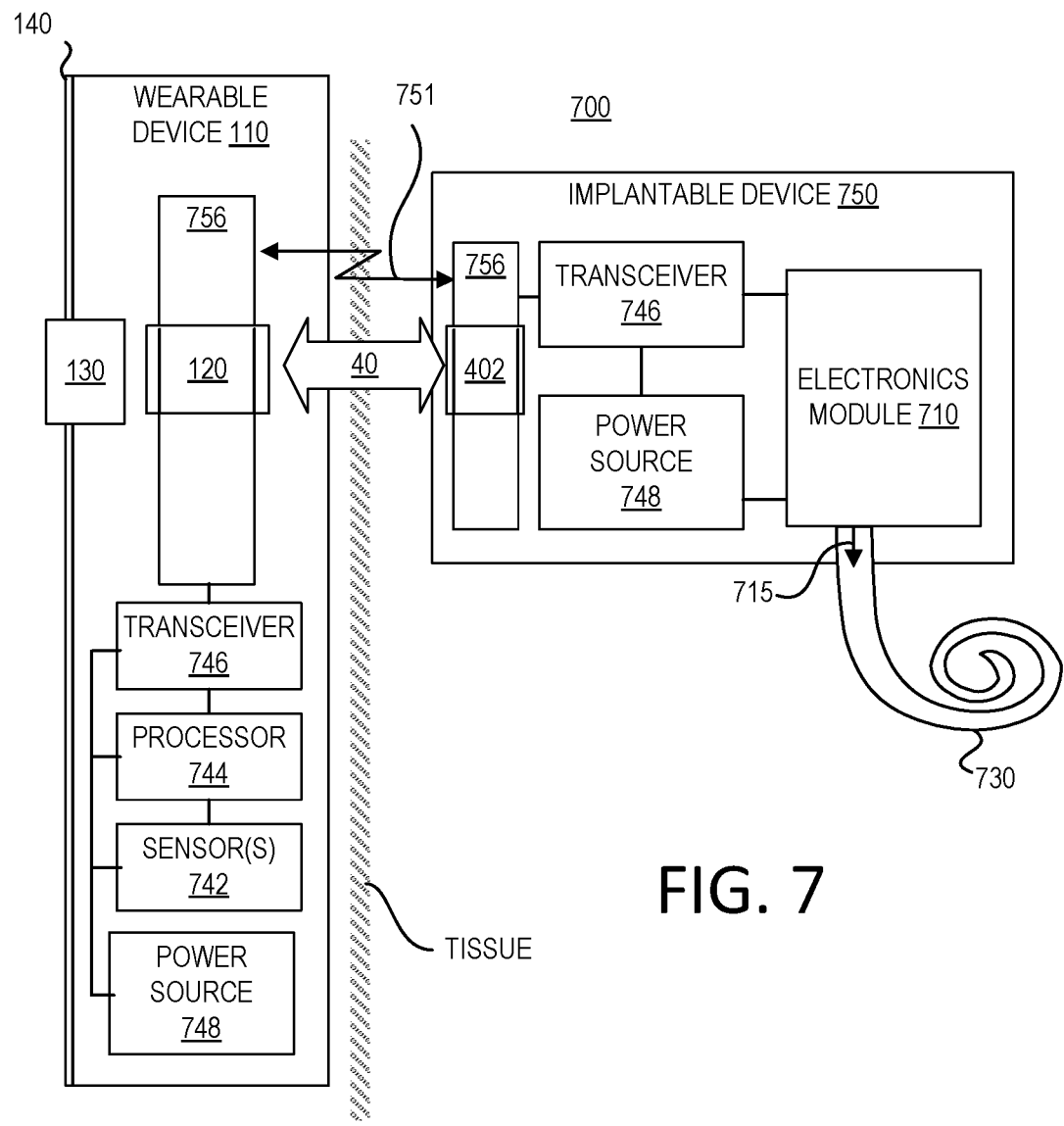
FIG. 7 is a functional block diagram of an implantable stimulator system that can benefit from the technologies described herein.

As previously described, the technology disclosed herein can be applied in any of a variety of circumstances and with a variety of different devices. Example devices that can benefit from technology disclosed herein are described in more detail in FIGS. 7-10, below. For example, the primary magnet set 120, the supplemental magnet set 130, and the cover 140 described herein can be part of a medical stimulation system 700, such as is shown in FIG. 7. In an example, the device 110 can be a wearable medical device, such as can be configured to be in communication with a cochlear implant as described in FIG. 8. As another example, the wearable device 110 can be part of a retinal prosthesis, such as is described in FIG. 9. In a further example shown in FIG. 10, the technology can used to retain an external component of a transcutaneous bone conduction system. The technology can be applied to other medical devices, such as neurostimulators, cardiac pacemakers, cardiac defibrillators, sleep apnea management stimulators, seizure therapy stimulators, tinnitus management stimulators, and vestibular stimulation devices, as well as other medical devices. These different systems and devices can benefit from the technology described herein.

Example Implantable Stimulation System

FIG. 7 is a functional block diagram of an implantable stimulator system 700 that can benefit from the technologies described herein. The implantable stimulator system 700 includes the wearable device 110 acting as an external processor device and an implantable device 750 acting as an implanted stimulator device. In examples, the implantable device 750 is an implantable stimulator device configured to be implanted beneath a recipient's tissue (e.g., skin). In examples, the implantable device 750 includes a biocompatible housing. Here, the wearable device 110 is configured to transcutaneously couple with the implantable device 750 via a wireless connection to provide additional functionality to the implantable device 750.

In the illustrated example, the wearable device 110 includes one or more sensors 742, a processor 744, a transceiver 746, and a power source 748. The one or more sensors 742 can be units configured to produce data based on sensed activities. In an example where the stimulation system 700 is an auditory prosthesis system, the one or more sensors 742 can include sound input sensors, such as a microphone, an electrical input for an FM hearing system, other components for receiving sound input, or combinations thereof. Where the stimulation system 700 is a visual prosthesis system, the one or more sensors 742 can include one or more cameras or other visual sensors. Where the stimulation system 700 is a cardiac stimulator, the one or more sensors 742 can include cardiac monitors. The processor 744 can be a component (e.g., a central processing unit) configured to control stimulation provided by the implantable device 750. The stimulation can be controlled based on data from the sensor 742, a stimulation schedule, or other data. Where the stimulation system 700 is an auditory prosthesis, the processor 744 can be configured to convert sound signals received from the sensor(s) 742 (e.g., acting as a sound input unit) into signals 751. The transceiver 746 is configured to send the signals 751 in the form of power signals, data signals, combinations thereof (e.g., by interleaving the signals), or other signals. The transceiver 746 can also be configured to receive power or data. Stimulation signals can be generated by the processor 744 and transmitted, using the transceiver 746, to the implantable device 750 for use in providing stimulation.

In the illustrated example, the implantable device 750 includes an electronics module 710, a stimulator assembly 730, a transceiver 746, a power source 748, and a coil 756. The implantable device 750 further includes a hermetically sealed, biocompatible housing enclosing one or more of the components.

The electronics module 710 can include one or more other components to provide auditory prosthesis functionality. In many examples, the electronics module 710 includes one or more components for receiving a signal and converting the signal into the stimulation signal 715. The electronics module 710 can further include a stimulator unit. The electronics module 710 can generate or control delivery of the stimulation signals 715 to the stimulator assembly 730. In examples, the electronics module 710 includes one or more processors (e.g., central processing units) coupled to memory components (e.g., flash memory) storing instructions that when executed cause performance of an operation. In examples, the electronics module 710 generates and monitors parameters associated with generating and delivering the stimulus (e.g., output voltage, output current, or line impedance). In examples, the electronics module 710 generates a telemetry signal (e.g., a data signal) that includes telemetry data. The electronics module 710 can send the telemetry signal to the wearable device 110 or store the telemetry signal in memory for later use or retrieval.

The stimulator assembly 730 can be a component configured to provide stimulation to target tissue. In the illustrated example, the stimulator assembly 730 is an electrode assembly that includes an array of electrode contacts disposed on a lead. The lead can be inserted into the recipient's cochlea. The stimulator assembly 730 can be configured to deliver stimulation signals 715 (e.g., electrical stimulation signals) generated by the electronics module 710 to the cochlea to cause a hearing percept in the recipient. In other examples, the stimulator assembly 730 is a vibratory actuator disposed inside or outside of a housing of the implantable device 750 and configured to generate vibrations. The vibratory actuator receives the stimulation signals 715 and, based thereon, generates a mechanical output force in the form of vibrations. The actuator can deliver the vibrations to the skull of the recipient in a manner that produces motion or vibration of the recipient's skull, thereby causing a hearing percept by activating the hair cells in the recipient's cochlea via cochlea fluid motion.

The transceivers 746 can be components configured to transcutaneously receive and/or transmit a signal 751 (e.g., a power signal and/or a data signal). The transceiver 746 can be a collection of one or more components that form part of a transcutaneous energy or data transfer system to transfer the signal 751 between the wearable device 110 and the implantable device 750. Various types of signal transfer, such as electromagnetic, capacitive, and inductive transfer, can be used to usably receive or transmit the signal 751. The transceiver 746 can include or be electrically connected to the coil 756.

The coils 756 can be components configured to receive or transmit a signal 751, typically via an inductive arrangement formed by multiple turns of wire. In examples, in addition to or instead of a coil, other arrangements can be used, such as an antenna or capacitive plates. The magnet sets 120 and 402 can be used to align respective coils 756 of the wearable device 110 and the implantable device 750. For example, the coil 756 of the implantable device 750 can be disposed in relation to (e.g., in a coaxial relationship) with the implantable magnet set 402 to facilitate orienting the coil 756 in relation to the coil 756 of the wearable device 110 via the magnetic connection 40. The coil 756 of the wearable device 110 can be disposed in relation to (e.g., in a coaxial relationship) with the primary magnet set 120.

The power source 748 can be one or more components configured to provide operational power to other components. The power source 748 can be or include one or more rechargeable batteries. Power for the batteries can be received from a source and stored in the battery. The power can then be distributed to the other components of the implantable device 750 as needed for operation.

As should be appreciated, while particular components are described in conjunction with FIG. 7, technology disclosed herein can be applied in any of a variety of circumstances. The above discussion is not meant to suggest that the disclosed techniques are only suitable for implementation within systems akin to that illustrated in and described with respect to FIG. 7. In general, additional configurations can be used to practice the methods and systems herein and/or some aspects described can be excluded without departing from the methods and systems disclosed herein.

Example Implantable Stimulation System—Cochlear Implant System

Figure 8:
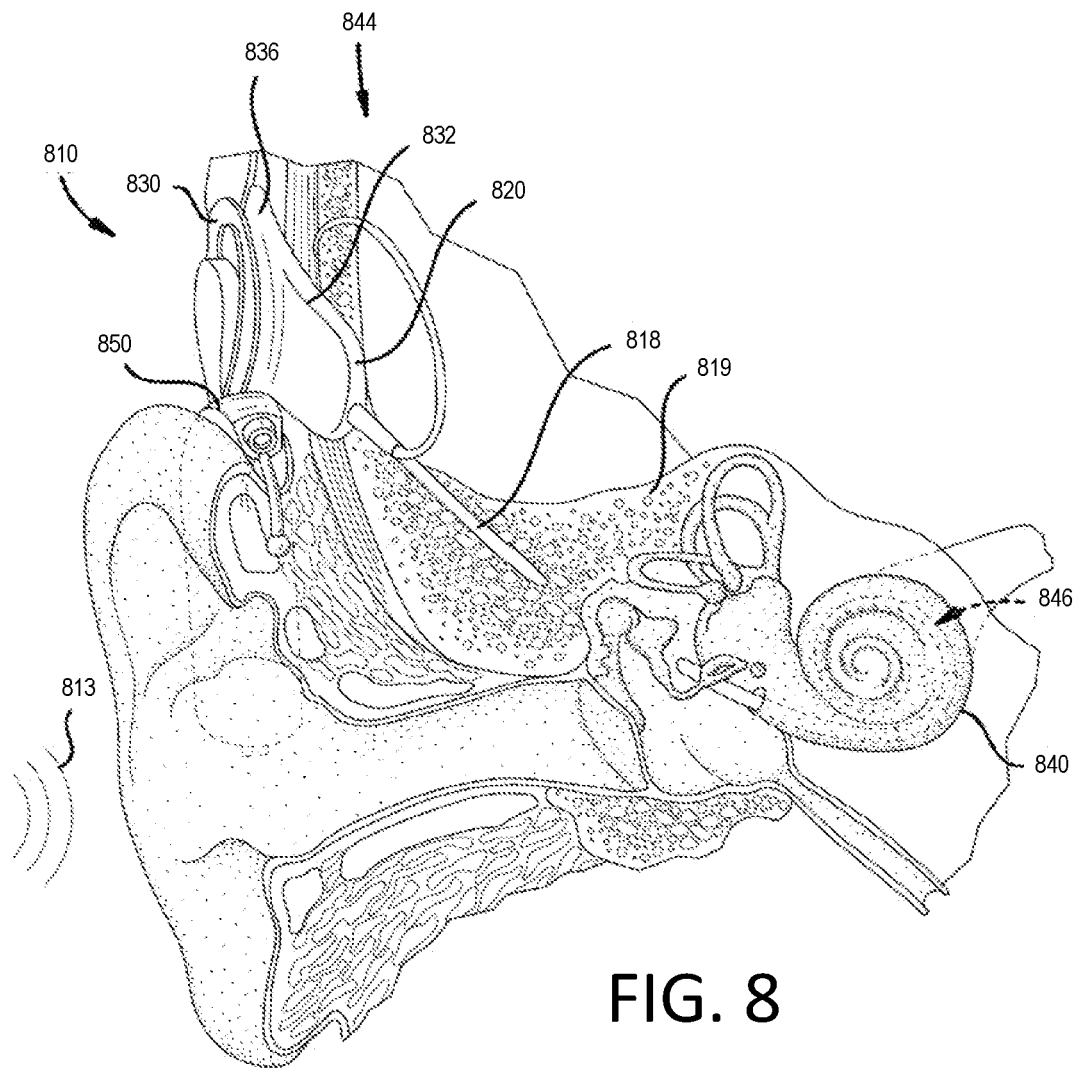
FIG. 8 illustrates an example cochlear implant system that can benefit from use of the technologies disclosed herein.

FIG. 8 illustrates an example cochlear implant system 810 that can benefit from use of the technologies disclosed herein. The cochlear implant system 810 includes an implantable component 844 (e.g., the implantable device 750) typically having an internal receiver/transceiver unit 832, a stimulator unit 820, and an elongate lead 818. The internal receiver/transceiver unit 832 permits the cochlear implant system 810 to receive signals from and/or transmit signals to an external device 850 (e.g., which can correspond to the wearable device 110). The external device 850 can be a button sound processor worn on the head that includes a receiver/transceiver coil 830 and sound processing components. Alternatively, the external device 850 can be just a transmitter/transceiver coil in communication with a behind-the-ear device that includes the sound processing components and microphone.

The implantable component 844 includes an internal coil 836, and preferably, an implanted magnet (such as implanted magnet 402, not shown in FIG. 8) fixed relative to the internal coil 836. The magnet can be embedded in a pliable silicone or other biocompatible encapsulant, along with the internal coil 836. Signals sent generally correspond to external sound 813. The internal receiver/transceiver unit 832 and the stimulator unit 820 are hermetically sealed within a biocompatible housing, sometimes collectively referred to as a stimulator/receiver unit. Included magnets (e.g., the primary magnet set 120 as supplemented by the supplemental magnet set 130) can facilitate the operational alignment of an external coil 830 and the internal coil 836 (e.g., via a magnetic connection 40 generated using techniques described herein), enabling the internal coil 836 to receive power and stimulation data from the external coil 830. The external coil 830 is contained within an external portion. The elongate lead 818 has a proximal end connected to the stimulator unit 820, and a distal end 846 implanted in a cochlea 840 of the recipient. The elongate lead 818 extends from stimulator unit 820 to the cochlea 840 through a mastoid bone 819 of the recipient. The elongate lead 818 is used to provide electrical stimulation to the cochlea 840 based on the stimulation data. The stimulation data can be created based on the external sound 813 using the sound processing components and based on sensory prosthesis settings.

In certain examples, the external coil 830 transmits electrical signals (e.g., power and stimulation data) to the internal coil 836 via a radio frequency (RF) link. The internal coil 836 is typically a wire antenna coil having multiple turns of electrically insulated single-strand or multi-strand platinum or gold wire. The electrical insulation of the internal coil 836 can be provided by a flexible silicone molding. Various types of energy transfer, such as infrared (IR), electromagnetic, capacitive and inductive transfer, can be used to transfer the power and/or data from external device to cochlear implant. While the above description has described internal and external coils being formed from insulated wire, in many cases, the internal and/or external coils can be implemented via electrically conductive traces.

Example Implantable Stimulation System—Retinal Prosthesis

Figure 9:
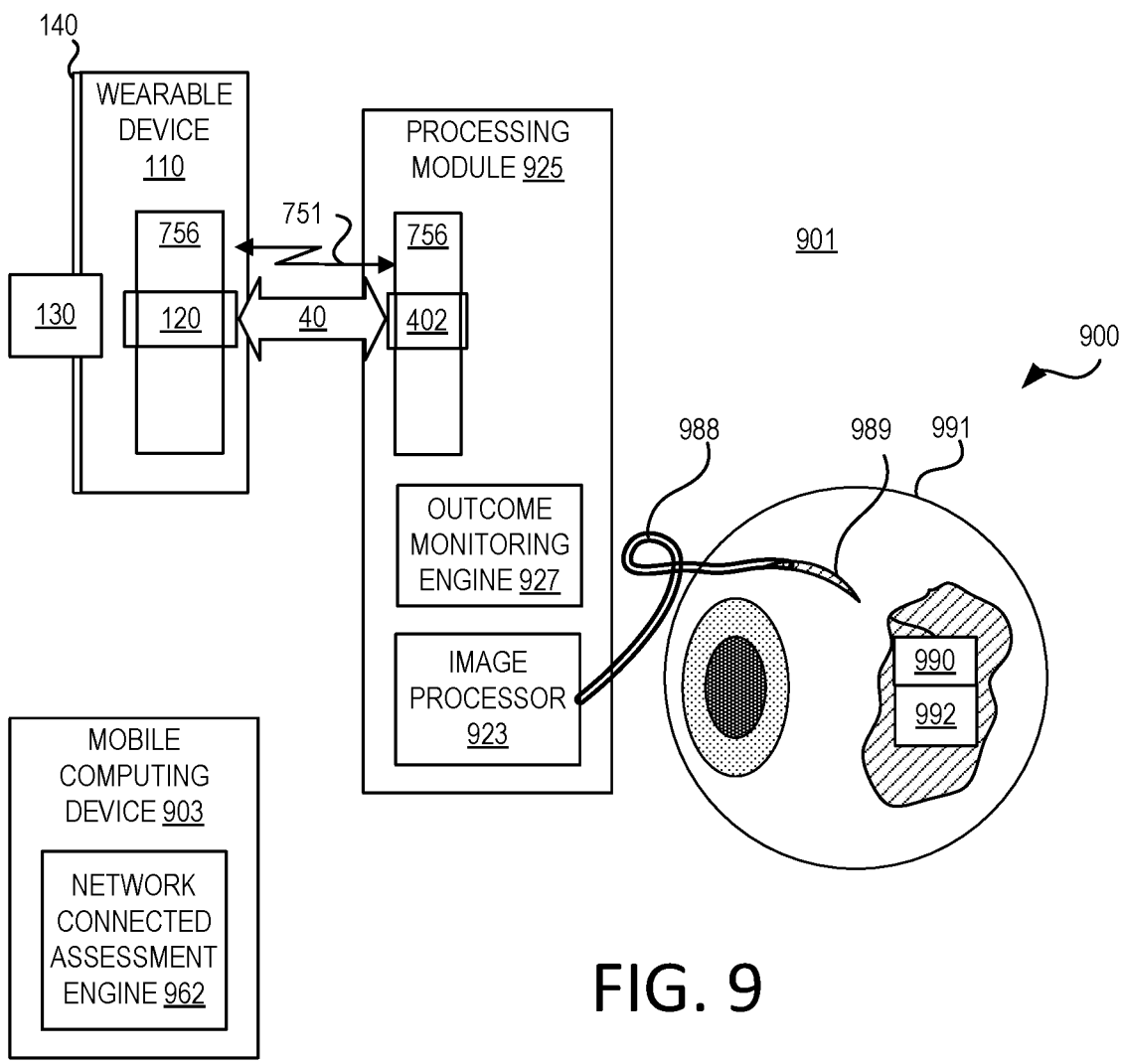
FIG. 9 illustrates a retinal prosthesis system that can benefit from use of the technologies disclosed herein.

FIG. 9 illustrates a retinal prosthesis system 901 that comprises, a wearable device 110, a retinal prosthesis 900 and a mobile computing device 903. The retinal prosthesis 900 comprises a processing module 925 (e.g. corresponding to the implantable device 750) and a retinal prosthesis sensor-stimulator 990 is positioned proximate the retina 991 of a recipient. The wearable device 110 and the processing module 925 can both include transmission coils 756 aligned via respective magnet sets. For example, the wearable device 110 includes a primary magnet set 120 as supplemented by a supplemental magnet set 130, and the implantable device includes an implantable magnet set 402. Signals 751 can be transmitted using the coils 756.

In an example, sensory inputs (e.g., photons entering the eye) are absorbed by a microelectronic array of the sensor-stimulator 990 that is hybridized to a glass piece 992 including, for example, an embedded array of microwires. The glass can have a curved surface that conforms to the inner radius of the retina. The sensor-stimulator 990 can include a microelectronic imaging device that can be made of thin silicon containing integrated circuitry that convert the incident photons to an electronic charge.

The processing module 925 includes an image processor 923 that is in signal communication with the sensor-stimulator 990 via, for example, a lead 988 which extends through surgical incision 989 formed in the eye wall. In other examples, processing module 925 can be in wireless communication with the sensor-stimulator 990. The image processor 923 processes the input into the sensor-stimulator 990, and provides control signals back to the sensor-stimulator 990 so the device can provide an output to the optic nerve. That said, in an alternate example, the processing is executed by a component proximate to, or integrated with, the sensor-stimulator 990. The electric charge resulting from the conversion of the incident photons is converted to a proportional amount of electronic current which is input to a nearby retinal cell layer. The cells fire and a signal is sent to the optic nerve, thus inducing a sight perception.

The processing module 925 can be implanted in the recipient and function by communicating with the wearable device 110, such as a behind-the-ear unit, a pair of eyeglasses, etc. The wearable device 110 can include an external light/image capture device (e.g., located in/on a behind-the-ear device or a pair of glasses, etc.), while, as noted above, in some examples, the sensor-stimulator 990 captures light/images, which sensor-stimulator is implanted in the recipient.

Similar to the above examples, the retinal prosthesis system 901 may be used in spatial regions that have at least one controllable network connected device associated therewith (e.g., located therein). As such, the processing module 925 includes a performance monitoring engine 927 that is configured to obtain data relating to a "sensory outcome" or "sensory performance" of the recipient of the retinal prosthesis 900 in the spatial region. As used herein, a "sensory outcome" or "sensory performance" of the recipient of a sensory prosthesis, such as retinal prosthesis 900, is an estimate or measure of how effectively stimulation signals delivered to the recipient represent sensor input captured from the ambient environment.

Data representing the performance of the retinal prosthesis 900 in the spatial region is provided to the mobile computing device 903 and analyzed by a network connected device assessment engine 962 in view of the operational capabilities of the at least one controllable network connected device associated with the spatial region. For example, the network connected device assessment engine 962 may determine one or more effects of the controllable network connected device on the sensory outcome of the recipient within the spatial region. The network connected device assessment engine 962 is configured to determine one or more operational changes to the at least one controllable network connected device that are estimated to improve the sensory outcome of the recipient within the spatial region and, accordingly, initiate the one or more operational changes to the at least one controllable network connected device.

Example Stimulation System—Transcutaneous Bone Conduction Device

Figure 10:
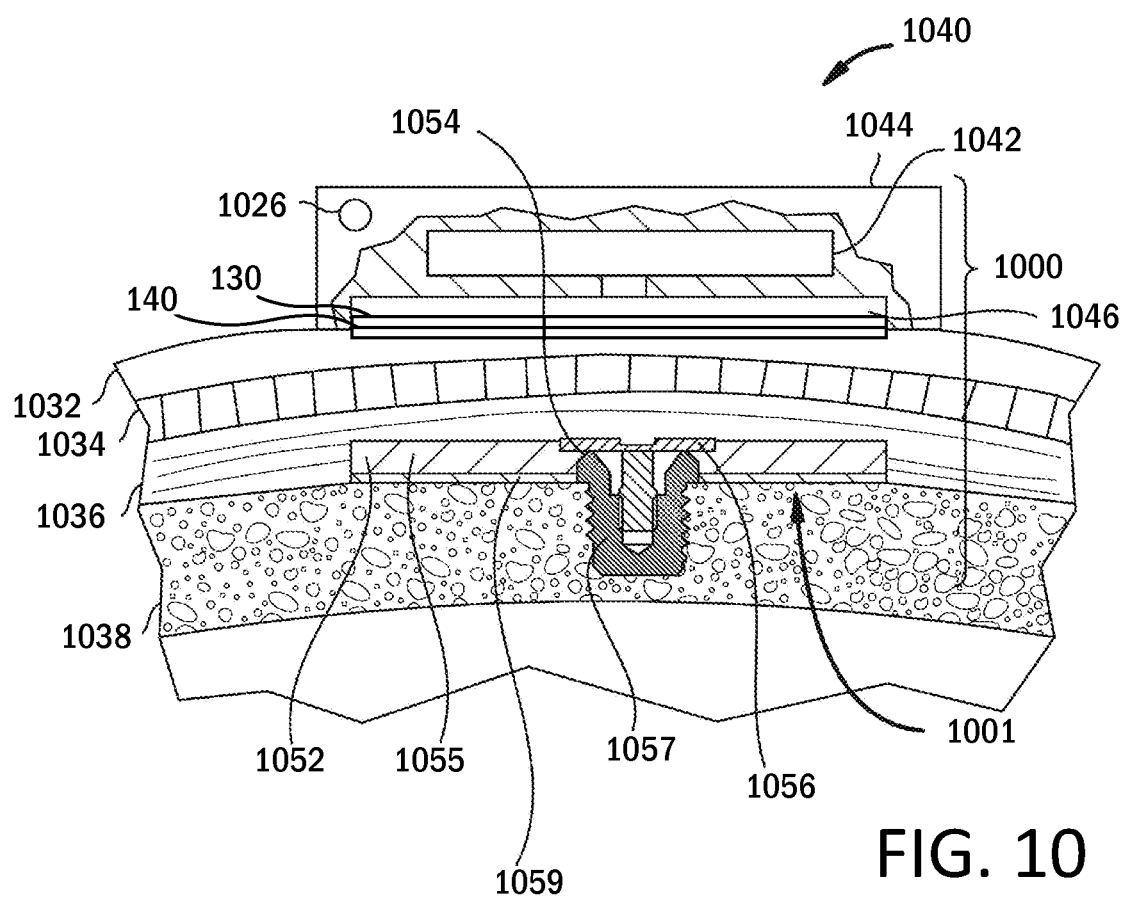
FIG. 10 illustrates a transcutaneous bone conduction device that can benefit from use of the technologies disclosed herein.

FIG. 10 illustrates an example of a transcutaneous bone conduction device 1000 having a passive implantable component 1001 that can benefit from use of the technologies disclosed herein. The transcutaneous bone conduction device 1000 includes an external device 1040 and an implantable component 1001. The implantable component 1001 includes a passive plate 1055 mounted on the bone 1038 and is transcutaneously coupled with a vibrating actuator 1042 located in a housing 1044 of the external device 1040. The plate 1055 can include or be in the form of a permanent magnet or in another form that generates or is reactive to a magnetic field, or otherwise permits the establishment of magnetic attraction between the external device 1040 and the implantable component 1001 sufficient to hold the external device 1040 against the skin 1032 of the recipient.

In an example, the vibrating actuator 1042 is a component that converts electrical signals into vibration. In operation, sound input element 1026 converts sound into electrical signals. Specifically, the transcutaneous bone conduction device 1000 provides these electrical signals to a vibrating actuator 1042, or to a sound processor component that processes the electrical signals, and then provides those processed signals to a vibrating actuator 1042. The manner in which the sound processor component processes the electrical signals can be modified based on auditory prosthesis settings. The vibrating actuator 1042 converts the electrical signals (processed or unprocessed) into vibrations. Because the vibrating actuator 1042 is mechanically coupled to the plate 1046, the vibrations are transferred from the vibrating actuator 1042 to the plate 1046. An implanted plate assembly 1052 is part of the implantable component 1050, and is made of a ferromagnetic material that may be in the form of a permanent magnet, that generates and/or is reactive to a magnetic field, or otherwise permits the establishment of a magnetic attraction between the external device 1040 and the implantable component 1050 sufficient to hold the external device 1040 against the skin 1032 of the recipient. Accordingly, vibrations produced by the vibrating actuator 1042 of the external device 1040 are transferred from plate 1046 across the skin 1032, fat 1034, and muscle 1036 to the plate 1055 of the plate assembly 1052. This may be accomplished as a result of mechanical conduction of the vibrations through the tissue, resulting from the external device 1040 being in direct contact with the skin 1032 and/or from the magnetic field between the two plates 1046, 1055. These vibrations are transferred without penetrating the skin 1032 with a solid object such as an abutment.

Technology described herein can be applied to replace or supplement the magnetic force of the plate 1046 or another component of the external device 1040. For example, a cover 140 can be configured to couple with the external device 1040 to accommodate a supplemental magnet set 130 that enhances a magnetic strength of the external device 1040. In an example, the cover 140 can be configured to couple with the plate 1046 (e.g., a skin facing side of the plate 1046 or a side of the plate 1046 opposite the skin-facing side) or with another component of the external device 1040.

As may be seen, the implanted plate assembly 1052 is substantially rigidly attached to a bone fixture 1057 in this example. But other bone fixtures may be used instead in this and other examples. In this regard, the implantable plate assembly 1052 includes a through hole 1054 that is contoured to the outer contours of the bone fixture 1057. The through hole 1054 thus forms a bone fixture interface section that is contoured to the exposed section of the bone fixture 1057. In an example, the sections are sized and dimensioned such that at least a slip fit or an interference fit exists with respect to the sections. A plate screw 1056 is used to secure plate assembly 1052 to the bone fixture 1057. The head of the plate screw 1056 can be larger than the hole through the implantable plate assembly 1052, and thus the plate screw 1056 positively retains the implantable plate assembly 1052 to the bone fixture 1057. The portions of plate screw 1056 that interface with the bone fixture 1057 substantially correspond to an abutment screw detailed in greater detail below, thus permitting the plate screw 1056 to readily fit into an existing bone fixture used in a percutaneous bone conduction device. In an example, the plate screw 1056 is configured so that the same tools and procedures that are used to install and/or remove an abutment screw from the bone fixture 1057 can be used to install and/or remove the plate screw 1056 from the bone fixture 1057. In some examples, there may be a silicone layer 1059 disposed between the plate 1055 and bone 1038.

As should be appreciated, while particular uses of the technology have been illustrated and discussed above, the disclosed technology can be used with a variety of devices in accordance with many examples of the technology. The above discussion is not meant to suggest that the disclosed technology is only suitable for implementation within systems akin to that illustrated in the figures. In general, additional configurations can be used to practice the processes and systems herein and/or some aspects described can be excluded without departing from the processes and systems disclosed herein.

This disclosure described some aspects of the present technology with reference to the accompanying drawings, in which only some of the possible aspects were shown. Other aspects can, however, be embodied in many different forms and should not be construed as limited to the aspects set forth herein. Rather, these aspects were provided so that this disclosure was thorough and complete and fully conveyed the scope of the possible aspects to those skilled in the art.

As should be appreciated, the various aspects (e.g., portions, components, etc.) described with respect to the figures herein are not intended to limit the systems and processes to the particular aspects described. Accordingly, additional configurations can be used to practice the methods and systems herein and/or some aspects described can be excluded without departing from the methods and systems disclosed herein.

Similarly, where steps of a process are disclosed, those steps are described for purposes of illustrating the present methods and systems and are not intended to limit the disclosure to a particular sequence of steps. For example, the steps can be performed in differing order, two or more steps can be performed concurrently, additional steps can be performed, and disclosed steps can be excluded without departing from the present disclosure. Further, the disclosed processes can be repeated.

Although specific aspects were described herein, the scope of the technology is not limited to those specific aspects. One skilled in the art will recognize other aspects or improvements that are within the scope of the present technology. Therefore, the specific structure, acts, or media are disclosed only as illustrative aspects. The scope of the technology is defined by the following claims and any equivalents therein.

What is claimed is:

1. An apparatus comprising:
   a wearable device having a primary magnet set of one or more magnets;
   a supplemental magnet set having one or more additional magnets and being configured to be selectively disposed proximate to the primary magnet set to enhance a magnetic strength; and
   a cover configured to couple with the wearable device, wherein the cover comprises an opening formed through a surface of the cover to expose the primary magnet set through the surface, and wherein the supplemental magnet set being configured to extend through the surface via the opening to be exposed to the primary magnet set.

2. The apparatus of claim 1, wherein the supplemental magnet set comprises at least one diametrically magnetized magnet.

3. The apparatus of claim 2, wherein the primary magnet set comprises at least four magnetic poles and/or wherein the supplemental magnet set comprises at least one radially-magnetized magnet.

4. The apparatus of claim 1, wherein the supplemental magnet set is disposed in a supplemental magnet case having a grip configured to facilitate removal of the supplemental magnet case from the wearable device, and wherein the grip extends at least partially across the surface of the cover, the surface facing away from the wearable device.

5. The apparatus of claim 1, wherein the supplemental magnet set is configured to be retained to the wearable device by a magnetic connection between the supplemental magnet set and the primary magnet set.

6. The apparatus of claim 1, wherein the supplemental magnet set is configured to be retained to the wearable device by a mechanical connection with the cover.

7. The apparatus of claim 1, wherein the wearable device comprises at least one microphone, and wherein the cover defines at least one microphone opening that at least partially overlaps with the at least one microphone, and the supplemental magnet set is offset from the at least one microphone.

8. The apparatus of claim 1, wherein the wearable device comprises an additional opening configured to receive the primary magnet set, and the additional opening and the opening overlap with one another to expose the primary magnet set and the supplemental magnet set to one another.

9. The apparatus of claim 1, wherein the primary magnet set is external to the opening.

10. The apparatus of claim 1, wherein the supplemental magnet set is disposed in a supplemental magnet case, and the opening of the cover is configured to receive the supplemental magnet case to receive the supplemental magnet set.

11. The apparatus of claim 1, wherein the supplemental magnet set extends at least partially external to the cover.

12. A kit comprising:
   a wearable device configured to selectively receive a selected primary magnet set;
   multiple primary magnet sets of varying magnetic strengths for use with the wearable device as the selected primary magnet set;
   at least one supplemental magnet set for use with the wearable device to supplement the selected primary magnet set; and a selected cover configured to selectively couple with the wearable device, wherein the selected cover comprises an opening formed through a surface of the selected cover to expose the selected primary magnet set through the surface, and wherein a selected supplemental magnet set of the at least one supplemental magnet set is configured to extend through the surface via the opening to be exposed to the selected primary magnet set.

13. The kit of claim 12, further comprising:
at least one accommodating cover for use as the selected cover and being configured to accommodate the selected supplemental magnet set when the selected supplemental magnet set is used to supplement the selected primary magnet set; and
at least one non-accommodating cover for use as the selected cover and being unable to accommodate the selected supplemental magnet set for use in supplementing the selected primary magnet set.

14. The kit of claim 13, wherein each of the at least one supplemental magnet set is disposed in a corresponding one of the at least one accommodating cover.

15. The kit of claim 13, wherein each of the at least one accommodating cover comprises an opening into which the selected supplemental magnet set can be at least partially received, and wherein each of the at least one non-accommodating cover lacks an opening into which the selected supplemental magnet set can be at least partially received, thereby being unable to accommodate the selected supplemental magnet set.

16. The kit of claim 15, wherein, when one of the at least one accommodating cover is coupled with a front of the wearable device and the selected primary magnet set is received within the wearable device, the selected primary magnet set is at least partially exposed through the opening of the at least one accommodating cover; and
wherein the wearable device defines a primary magnet opening at a back of the wearable device through which the selected primary magnet set can be received by the wearable device.

17. A method comprising:
establishing a first magnetic connection between an implanted magnet set and a primary magnet set housed by a device;
coupling a cover to the device, wherein the cover comprises an opening formed through a surface of the cover to expose the primary magnet set through the surface;
positioning a supplemental magnet set to extend through the surface of the cover via the opening to expose the supplemental magnet set and the primary magnet set with one another to supplement the primary magnet set with the supplemental magnet set; and
establishing a second magnetic connection between the implanted magnet set and the primary magnet set as supplemented by the supplemental magnet set, wherein the second magnetic connection is stronger than the first magnetic connection.

18. The method of claim 17, further comprising:
removing the cover; and
coupling an additional cover to the device.

19. The method of claim 18, wherein the additional cover comprises an additional opening formed through an additional surface of the cover to expose the primary magnet set through the additional surface, and the method further comprises:
positioning the supplemental magnet set to extend through the additional surface of the additional cover via the additional opening to expose the supplemental magnet set and the primary magnet set with one another to supplement the primary magnet set with the supplemental magnet set.

20. The method of claim 18, further comprising:
selecting the additional cover from a plurality of supplemental covers that are each associated with a different magnetic strength.

* * * * *